Nov. 12, 1946. V. SCARTH Re 22,811
EXTRACTIVE DISTILLATION WITH FURFURAL
Original Filed Dec. 21, 1944
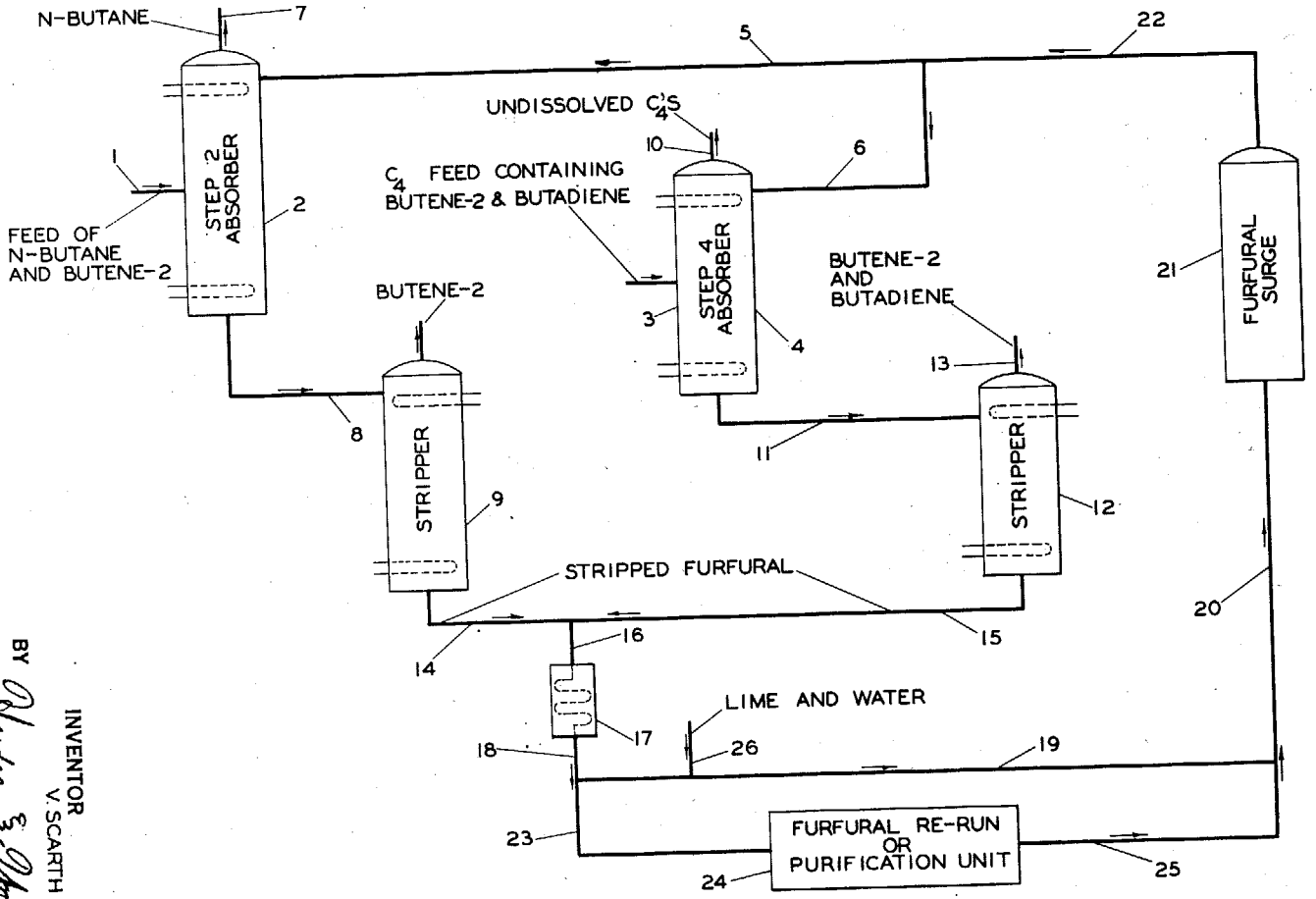
INVENTOR
V. SCARTH
BY Hudson & Young
ATTORNEYS Reissued Nov. 12, 1946 Re. 22,811

UNITED STATES PATENT OFFICE 22,811

EXTRACTIVE DISTILLATION WITH FURFURAL

Virgil Scarth, Bartlesville, Okla., assignor to Phillips Petroleum Company, a corporation of Delaware Original No. 2,404,253, dated July 16, 1946, Serial No. 569,243, December 21, 1944. Application for reissue August 9, 1946, Serial No. 689,319

6 Claims. (Cl. 196—13)

This invention relates to extractive distillation, more particularly to extractive distillation of hydrocarbon streams containing unsaturated hydrocarbons using furfural as the solvent, and still more particularly to extractive distillation for the recovery of aliphatic monoolefins and/or aliphatic conjugated diolefins especially normal butene and/or butadiene from hydrocarbon streams containing same with furfural as the solvent.

It has become customary to recover unsaturated aliphatic hydrocarbons especially butene and/or butadiene from hydrocarbon streams containing them by extractively distilling the stream in a fractional distillation column or absorber into the top of which there is introduced continuously a stream of furfural, usually containing a few per cent of dissolved water, in amount sufficient to dissolve the unsaturated hydrocarbon. The top of the column is refluxed with a portion of condensed overhead vapors in the usual way and the bottom of the column is provided with the conventional reboiler for the purpose of boiling the rich furfural as it attains the bottom so as to free it from undesired paraffin and/or olefin. The rich furfural is withdrawn and fed to a stripping column where the dissolved unsaturated hydrocarbon is removed. The stripper is provided with reboiler and is refluxed with a portion of the condensed overhead. The purpose of refluxing the absorber and stripper is to prevent carryover of furfural into the overhead vapors. The stripped furfural is then returned from the bottom of the stripper to the absorber.

During extractive distillation of unsaturated hydrocarbons with furfural the furfural becomes contaminated with acids, polymer and other impurities which are very deleterious because they are highly corrosive to the metal equipment. The resulting corrosion of expensive equipment including fractional distillation columns and accessories such as piping, reboilers, condensers, accumulators, pumps and so forth presents a serious problem for which various remedies have been proposed none of which is entirely satisfactory, so far as I am aware. The cause of the formation of corrosive impurities in the furfural is not known even though the problem has been extensively investigated. Factors which may contribute to the formation include high temperature, presence of water and presence of unsaturated hydrocarbons. It is believed by some investigators that the furfural selectively absorbs traces of corrosive material from the hydrocarbon feed or of material from the feed which becomes corrosive upon reacting with the furfural.

It is not desired to be limited to any theory as to the cause of the furfural becoming corrosive.

It is conventional practice to purify the furfural continuously by "re-running" a side stream of the furfural leaving the stripper and recycled to the absorber. This is carried out in accordance with U. S. Patents to K. H. Hachmuth 2,372,668 and 2,350,609, and Buell et al. 2,350,584. However, there is considerable additional loss of furfural during the re-running operation. A large portion of this loss is due to polymerization of the furfural in the re-run unit. At present the furfural is re-run for the purpose of removing other corrosive material as well as the polymer. If a feasible method of preventing the accumulation of corrosive material in the furfural in the main system (i. e., in the absorbing and stripping operations) were available, the amount of furfural passed to the re-run unit could be materially decreased with many advantages principal of which is the reduction of polymerization of furfural in the re-running operation. Many other advantages of such a method will appear hereinafter.

The principal object of the present invention is to provide an improved method of conducting extractive distillation of unsaturated hydrocarbons with furfural. Another object is to provide a feasible method of preventing the accumulation of corrosive material in the furfural in an extractive distillation system wherein unsaturated hydrocarbons especially aliphatic monoolefins and diolefins are separated from hydrocarbon streams containing same. Another object is to provide such an extractive distillation system applied to the recovery of normal butene and/or butadiene by means of furfural. Another object is to provide a method which greatly reduces the amount of furfural which has to be passed to the re-run unit. Another object is to prevent corrosion of the main system (i. e., the extractive distillation system proper as distinguished from the re-run unit). Another object is to reduce the loss of furfural in the extractive distillation system and in the re-running operation. Another object is to prevent the formation of corrosive impurities in the furfural at the point where those impurities are most deleterious. Another object is to accomplish the foregoing objects in a manner which does not cause foaming of the furfural. Numerous other objects will hereinafter appear.

The accompanying drawing portrays diagrammatically one arrangement of equipment for carrying out the present invention.

I have discovered that in the extractive distillation of hydrocarbon streams with furfural as the solvent to recover unsaturated hydrocarbons therefrom the furfural may be prevented from becoming corrosive and from corroding the equipment by intimately contacting the furfural in the extractive distillation system with lime. The term "lime" as used herein denotes calcium hydroxide. I have determined that limestone will not operate in the process of the present invention.

The contacting of the furfural with the lime is commonly accomplished by introducing the lime in finely divided form into the furfural in any suitable manner. The lime may be added in the dry form, as a dispersion or slurry in furfural, as a dispersion or slurry in water or by other methods. Probably the most convenient method is to add it in the form of a suspension or dispersion in a portion or all of the makeup water which is commonly added continuously to the furfural fed to the absorber or absorbers in order to impart the desired content of dissolved water to the furfural. It will be understood that addition of make-up water is for the purpose of replacing water volatilized from the furfural in the absorbers and strippers. The use of furfural containing dissolved water as a solvent in the extractive distillation of normal butene and/or butadiene is disclosed and claimed in the copending application of K. H. Hachmuth, Ser. No. 438,844, filed April 13, 1942.

The present invention is applied to the extractive distillation of unsaturated hydrocarbons with furfural wherever the furfural becomes corrosive due to conditions prevailing in the extractive distillation system. The factors which cause the furfural to become corrosive are but little understood but it is believed that they include the high temperatures especially in the reboiling sections of the absorber and stripper, the presence of water and unsaturated hydrocarbons especially olefins and diolefins, the presence of air or oxygen. The development of corrosivity in the furfural is accompanied by the formation of polymer which represents a loss of furfural and causes poor heat transfer and other troubles. The present invention is especially applicable to the extractive distillation of butadiene and/or normal butene with furfural, this being the principal if not the only commercial application of extractive distillation with furfural as a means of recovering unsaturated hydrocarbons. However, it may also be applied where furfural is used in the recovery by extractive distillation of other aliphatic olefins or aliphatic conjugated diolefins from hydrocarbon streams containing the same.

The conversion of normal butane to butadiene is now commonly effected by a series of steps including (I) catalytic dehydrogenation of normal butane to normal butene, (II) recovery of normal butene and recycle normal butane by first fractionally distilling the $C_4$ content of the effluent from step I in a butene-1 column wherein butene-1 is recovered overhead followed by extractive distillation of the resulting bottoms fraction of n-butane and butene-2 with furfural to separate the butene-2 from the normal butane which is recycled to step I, (III) passing the combined butene-1 and butene-2 recovered in step II to a second catalytic stage and therein dehydrogenating same to butadiene, and finally (IV) recovering butadiene from the $C_4$ content of the effluent of step III by a sequence of steps including depropanizing, debutanizing, extractive distillation of the debutanizer overhead with furfural whereby the butadiene and butene-2 content are dissolved in the furfural and subsequently recovered therefrom by the stripping operation, and finally fractionally distilling the butadiene-butene-2 mixture to separate pure butadiene from butene-2. This process is fully described in the copending application of K. H. Hachmuth, Ser. No. 481,305, filed March 31, 1943, which has now matured into Patent No. 2,386,310, dated Oct. 9, 1945. The present invention is applicable to the furfural extractive distillation system in step II or in step IV or in both. Or it may be applied in those butadiene plants where normal butylene feed is catalytically dehydrogenated to butadiene and butadiene is recovered from the effluent by extractive distillation with furfural.

In such an extractive distillation process the furfural enriched in unsaturated hydrocarbon is withdrawn from the bottom of the absorber and passed to the stripper where the unsaturated hydrocarbon is stripped therefrom. The stripped furfural is then cooled and after addition of make-up water is recycled to the absorber. Usually a surge tank is provided in the recycle line. A sidestream of the stripped furfural is continuously fed to a furfural re-run unit wherein it is steam distilled, e. g. in the manner of Buell et al. 2,350,584, to give a purified material consisting essentially of furfural and dissolved water and free from polymer and other material relatively non-volatile with steam. The re-run furfural is then merged with the main recycle stream for passage to furfural storage and ultimately to the absorber. The volume of furfural passed to the re-run unit is preferably such as to maintain the concentration of polymer in the furfural in the system at below 1% by weight.

In accordance with the present invention lime is admixed with the furfural in the extractive distillation system, for example, by suspending it therein in any suitable way. It is preferred to limit the amount of lime to that required to keep the acidity at the desired level. The amount of lime required is so small that in practice no difficulty due to sedimentation of the lime or its reaction products is encountered. The lime or a portion thereof may dissolve in the furfural; the presence of dissolved water in the furfural may enhance any such tendency.

A very convenient method of contacting the furfural with the lime is to employ an excess of a dispersion of lime in water, admix it very intimately with the furfural in any suitable way, for example, by means of a centrifugal mixing pump, run the resulting churned-up mixture or emulsion into a settling tank where it is allowed to separate into two layers, an upper layer of the water and lime which have not dissolved in the furfural and a lower layer of furfural which is saturated with water and which may contain dissolved lime. These layers are separately withdrawn, the water layer being recycled to the mixing zone to save its water, lime and dissolved furfural content and the furfural layer being fed to the absorber. Under conditions where corrosiveness of the furfural in the system can be kept down to a satisfactory level such a treatment as just outlined may be applied to a sidestream of the recycle furfural, the resulting non-corrosive furfural being intimately admixed with the balance of the recycle furfural and the furfural from the re-run unit and allowed to stand as in a surge or storage tank for a period of time before being re-introduced to the absorber.

Alternatively an excess of powdered lime may be intimately admixed with the furfural and after a suitable period of time separated therefrom by any suitable means such as filtration, centrifuging or sedimentation.

It is preferred to introduce enough lime into the furfural to reduce the acid content of the furfural in the extractive distillation system below 0.06 per cent by weight, measured as acetic acid, and still more preferably below 0.04 per cent by weight. I have found that below 0.04 per cent of acidity no appreciable corrosion occurs; between 0.04 and 0.06 per cent acidity the concentration of the corrosive substance whatever it is may or may not be such that serious corrosion occurs, apparently depending upon factors not understood at present; while, at an acidity above 0.06 per cent corrosion always occurs and is usually so high that the equipment, especially the fractionating columns (i. e. the absorbers) and the strippers, would soon be eaten away below the point of safe operation if the plant continued to operate at such levels of acidity. Furthermore, the loss of furfural by polymerization at levels of acidity above 0.06 per cent becomes excessive so that furfural consumption exceeds the available supply which is exceedingly dangerous to the synthetic rubber program. The relationship between level of acidity and polymerization of furfural is at present not understood and I do not wish to be limited to any theory with regard thereto.

It is preferred to introduce the lime to the furfural at a point in the system such that the furfural is at a temperature of not over 130° F. at the point where the admixture takes place. Usually the coldest point in the furfural system is just after the cooler or coolers which are employed to cool the furfural leaving the stripper or strippers and so it is preferred to add the lime at this point. The reason for adding the lime at a point of low temperature is that the possibility of additional polymerization of furfural upon the introduction of lime to hot furfural is thereby eliminated.

The purpose of lime addition is to reduce the acid content of the furfural, reduce the formation of polymer and the corrosiveness of the furfural. The manner in which these several factors are inter-related is not understood but it has been definitely established that the addition of lime does prevent the furfural from being corrosive and does reduce the polymer formation, whether one causes the other or not. The present invention may be employed from the start of operations to keep the furfural in the system from ever becoming corrosive or may be applied to systems in which the furfural has become corrosive to eliminate the corrosivity and keep the system thenceforth non-corrosive. Thus the process of the present invention prevents non-corrosive furfural from becoming corrosive and also prevents corrosive furfural from exerting its deleterious action. The addition of lime in accordance with the present invention involves more than simple neutralization of corrosive acidity since it inhibits polymer formation as well. Moreover, it has been found by experimental work that neither the acid content nor the pH of furfural is necessarily an index of its corrosiveness. It will be obvious that acid content and pH are not the same since it is common to have a high acid content associated with a pH ranging from 0 to 7 or a low acid content and a pH ranging from 0 to 7.

As indicated above, the acid content of the furfural is not necessarily an absolute index of its corrosiveness. It is believed that the concentration of corrosive material in the furfural increases somewhat in proportion to the acidity. At levels of acidity greater than 0.04 per cent it is evident that some factor other than acidity comes into play as a cause of corrosion since between levels of 0.04 and 0.06 per cent acidity serious corrosion may or may not occur and at levels of acidity above 0.06 per cent the corrosion which occurs is not always serious although it usually is. In any event, whatever the causes of corrosion and regardless of theory it has been proven absolutely that by addition of lime to the furfural in the system in an amount such as to reduce the acidity to, or maintain the acidity at, levels below 0.04 per cent serious corrosion is prevented and polymerization is inhibited; while reduction of acidity to, or maintenance at, levels between 0.04 and 0.06 per cent by the addition of lime in most cases prevents serious corrosion and reduced polymerization of furfural to satisfactory levels.

In accordance with the present invention the acid content may be reduced nearly to or to the neutral point or the furfural may be made alkaline although the latter practice is not ordinarily followed because the tendency of furfural to polymerize is enhanced under alkaline conditions. It is preferred to add only enough lime to reduce the acid content below 0.06 per cent and preferably below 0.04 per cent which practically eliminates corrosion of carbon steel by the furfural, however, the nearer the neutral point or the point of zero acidity the less polymers of furfural will be formed. When the acid content of furfural in the main system is below 0.04 per cent the corrosion of carbon steel equipment is negligible and the rate of formation of polymer is substantially lower than when the acid content is above 0.06 per cent.

The products formed from the reaction of lime are removed from the system in the re-run unit with the polymers, so no problem due to accumulation of lime or its reaction products is encountered. In ordinary operation the re-running is carried out at such a rate that the furfural in the entire system is re-run in a short time say every two to three days. If enough lime is added to cause a sediment to form in the main system it may be necessary to provide a trap or filter to remove the sediment from the furfural. My invention may be applied by adding lime to a small side stream of furfural and any sediment that might be formed may be removed by filtering or some other method before the furfural is returned to the main stream. However, it is often desirable to add only enough lime to reduce the acid content of the furfural to the extent indicated but not enough to result in difficulties due to lime or the reaction products of lime settling in the system.

In accordance with my invention the fresh furfural which is added as makeup to the system may be treated with lime prior to its introduction into the extractive distillation system.

In accordance with the present invention lime is added in the main system, i. e. in the extractive distillation system proper, as distinguished from the re-run unit. The addition of lime to the re-run unit is disclosed and claimed in my copending application Ser. No. 607,212, filed July 26, 1945.

It is often desirable to apply the present invention to extractive distillation systems wherein furfural has become excessively corrosive. In such case it may be desirable to add enough furfural in the main system to reduce the acidity 0.02 per cent each day until it is below 0.04 per cent and to then reduce the amount of lime added to a figure which will hold the acidity at this level.

Referring to the accompanying drawing, I have illustrated diagrammatically the application of my invention to a plant in which butadiene is made by the two-stage catalytic dehydrogenation of normal butane. The mixture of normal butane and butene-2 recovered from step I of the process enters absorber 2 via line 1, while the $C_4$ hydrocarbons derived from step III and containing butene-2 and butadiene enter absorber 4 via line 3. Absorbers 2 and 4 carry out the extractive distillation of the feed with furfural injected into the top via lines 5 and 6, respectively. Absorbers 2 and 4 are provided with conventional reboiling means and means for condensing and returning a portion of the overhead as reflux, the latter being indicated diagrammatically by a cooling coil in the top of each absorber. The undissolved normal butane leaves absorber 2 via line 7, while the furfural rich in butene-2 is withdrawn as bottom product via line 8 and fed to stripper 9 where the dissolved butene-2 is driven off. Stripper 9 is likewise provided with conventional reboiler and means for condensing and returning a portion of the overhead as reflux.

The undissolved $C_4$ hydrocarbons leave absorber 4 via line 10 while the furfural rich in butene-2 and butadiene passes via line 11 to stripper 12 which performs the same function as stripper 9, the butene-2 and butadiene mixture leaving via line 13. The stripped furfural streams, leaving stripper 9 via line 14 and stripper 12 via line 15, are merged and fed via line 16 to cooler 17. It will be understood that a cooler may be provided for each stripped furfural stream if desired. The cooled furfural flowing in line 18 is passed via lines 19 and 20 to furfural surge or storage 21 whence it is recycled via line 22 and lines 5 and 6 to the absorbers. A side stream of furfural is passed via line 23 to the re-run unit 24 where it is continuously purified, in the manner now well known in the art, to remove the polymer therefrom. The re-run furfural is passed via line 25 into the main recycle stream in line 19.

In accordance with the present invention lime is continuously fed in the proper amounts indicated above into the main recycle stream flowing in line 19. This is accomplished by means of line 26 which, it will be understood, is purely diagrammatic. Usually both lime and water are injected into the stream in line 19. As explained above it is often convenient to inject the make-up water at this point. A point of injection of lime close to cooler 17 is preferred because the temperature is at substantially the lowest level at this point and because this gives a relatively long line between the point of injection of lime and furfural surge 21. Intimate mixing of the lime with furfural may take place in the long pipe indicated by lines 19 and 20.

It will be understood that the showing in the drawing is purely diagrammatic and that the lime and water may be added separately or in any desired manner and that provision may be made for the removal of any excess lime or sediment. It may or may not be necessary to provide for the removal of the reaction products of lime and the impurities in the furfural, depending upon the amount of lime added and the rate at which furfural is passed to the re-run unit 24 for purification.

*Example*

In the manufacture of butadiene by two-stage dehydrogenation of normal butane, a recovery system, as shown in the drawing, was employed. Furfural was fed continuously into the absorbers 2 and 4 at the rate of 260,000 gal./hr. entering both absorbers. The furfural contained 6% of water by weight based on the weight of furfural and water. The stripped furfural from both strippers was cooled to 120–130° F. and the major part of the cooled product was passed to the surge tank 21. A side stream of 3500 gal./hr. was withdrawn via line 23 and fed to re-run unit 24. The total volume of furfural in the entire system was 225,000 gallons. The acidity of the furfural in the main system was 0.10 weight per cent measured as acetic acid. This was exceedingly corrosive to the equipment and polymer formation was excessive. The acidity had been approximately 0.10% for ten days, during which time the polymer content increased from 0.4 to 1.5 per cent by weight. Under these conditions, namely at 0.10% acidity, 1.5% polymer concentration and 3500 gal./hr. of furfural re-run, equilibrium had been established. However, operations were unsatisfactory and it was considered imperative to reduce corrosion and polymerization because otherwise the plant would be corroded away in a short time and it would be impossible to obtain sufficient furfural to continue operations.

Under the foregoing conditions, lime was added to the furfural in the main system at a rate of 11 lbs./hr. The lime was added in the form of a slurry in the makeup water which was employed to keep the water concentration at approximately 6%. The slurry was admixed with the furfural recycle stream immediately after the cooler, as shown in the drawing. The acidity immediately began to decrease at the rate of approximately 0.015% per day. When the acidity reached 0.04% the rate of addition of lime was decreased to 6 lbs./hr. and the acidity varied from 0.03 to 0.038% from then on for an indefinite period. The polymer content had decreased to 0.3% and remained at about this figure. Simultaneously with the attainment of 0.04% acidity, the rate of re-running of furfural was reduced to 2000 gal./hr. which sufficed to keep the polymer concentration from increasing above 0.3%.

As a result of the use of lime in the manner described in the foregoing example the loss of furfural in the plant was reduced from 4000 to 1500 gal./day.

The amount of lime necessary to be added to the furfural in accordance with the present invention in order to keep the furfural from becoming corrosive and the polymer content thereof from increasing is extremely small. Under ordinary conditions of operation, it ranges from 0.000005 to 0.000006 lbs./gal. of furfural fed into the absorber per hour. Thus, the total pounds of lime in the system at any one time is very small, usually less than 1000 lbs. for a system containing 225,000 gallons furfural as in the example.

From the foregoing, many advantages of the present invention will be apparent to those skilled in the art. The principal advantage is that corrosion of the equipment in the main system is prevented. This allows the use of equipment of carbon steel which is much less expensive than corrosion-resistant metals. Another major advantage of the present invention is that it inhibits polymer formation in the main system which of itself gives rise to many advantages well known to those skilled in the art. The invention accomplishes simultaneous reduction in the level of acid concentration in furfural in the extractive distillation system and reduction in the rate of polymerization of furfural. The invention is simple and can be carried out without requiring expensive additional equipment or introducing complications into the existing extractive distillation system and re-run unit. By using lime, there is no danger of high concentration of alkaline material at any point which would be harmful because it would cause an unduly high rate of polymerization of furfural; lime is unable to give a highly alkaline condition by reason of its nature and limited solubility in furfural. The invention is extremely economical to apply because of the small amount of lime and because lime is cheap. The invention greatly reduces the amount of furfural which has to be re-run in order to remove polymer. This reduction in amount of furfural re-run gives rise to many other advantages, the principal of which is the markedly reduced loss of furfural and the lowered cost of re-running the smaller amount of furfural. It will be understood by those skilled in the art that loss of furfural in the re-run system is high because the re-running itself causes additional polymerization and because it is necessary to leave a considerable amount of furfural in the polymer in order to get it out of the re-run unit.

The invention is further advantageous in that it accomplishes prevention of formation of impurities at the very point where such impurities are most deleterious, namely in the extractive distillation system which embodies very expensive absorber and stripper units. A very marked advantage of the present invention is that it causes no foaming of the furfural in the extractive distillation system. Foaming of furfural in the absorbers and strippers is most objectionable. The behavior of lime introduced in accordance with the present invention is to be compared with that of soda ash, sodium bicarbonate or sodium hydroxide. Undoubtedly such sodium compounds would, if added to the furfural in the main system, substantially decrease corrosion and formation of polymers; however, such alkaline-reacting alkali metal compounds cause the furfural to foam which cannot be tolerated in processes of absorption and stripping. Even traces of sodium hydroxide, carbonate or bicarbonate cause foaming of furfural so that it would be completely impossible to use such materials in place of lime in accordance with the present invention.

Another advantage of the present invention is that the amount of lime required is so small that no problem due to sediment in the main system is presented. The lime or its reaction products is completely removed from the furfural in the re-running operation. Many other advantages of the process of the present invention will be apparent to those skilled in the art.

I claim:

1. In the process of separating unsaturated aliphatic hydrocarbons from a mixed hydrocarbon stream containing such unsaturates by extractive distillation wherein said mixed hydrocarbon stream is passed upward through an absorber tower in countercurrent to a descending stream of solvent composed of furfural containing dissolved water, a bottoms product consisting of furfural rich in unsaturated hydrocarbon is withdrawn from said absorber tower, said bottom product is introduced into a stripper column and there stripped of its unsaturated hydrocarbon content, a bottoms product consisting of stripped furfural is withdrawn from said stripper column and split into two streams, one of such resulting streams is passed to a re-run unit and there distilled to give a purified material consisting essentially of furfural and water dissolved therein, the purified furfural is combined with the other stream of stripped furfural and the resulting combined furfural stream is recycled to said absorber tower as solvent for the extractive distillation step; tnat improvement which consists of simultaneously inhibiting polymerization of furfural, corrosion of equipment due to acids and corrosion of equipment due to factors other than acidity by introducing lime into that branch of the stripped furfural stream which bypasses the said re-run unit, at a point between the place where said stripped furfural stream is split and the place where the recycled stripped furfural is fed into said absorber tower; and controlling the amount of lime so introduced so that the acidity of the furfural in the extractive distillation system is maintained between 0.02 per cent and 0.06 per cent by weight, calculated as acetic acid.

2. The process of claim 1 wherein the lime is introduced into the furfural in the form of an aqueous dispersion.

3. The process of claim 1 wherein the introduction of said lime is accomplished by admixing same with said branch of the stripped furfural stream which bypasses the re-run unit while said furfural is at a temperature of not over 130° F.

4. The process of claim 1 wherein said hydrocarbon stream is an aliphatic $C_4$ stream and wherein said unsaturated hydrocarbon is an aliphatic $C_4$ hydrocarbon.

5. The process of claim 1 wherein said unsaturated hydrocarbon comprises butene-2.

6. The process of claim 1 wherein said unsaturated hydrocarbon comprisese butadiene.

VIRGIL SCARTH.